United States Patent [19]
van der Wal

[11] Patent Number: 5,273,544
[45] Date of Patent: Dec. 28, 1993

[54] INJECTION DEVICE

[75] Inventor: Gillis P. van der Wal, Olst, Netherlands

[73] Assignee: Duphar International Research B.V., Weesp, Netherlands

[21] Appl. No.: 896,310

[22] Filed: Jun. 10, 1992

[30] Foreign Application Priority Data

Jun. 13, 1991 [EP] European Pat. Off. ........ 91201469.3

[51] Int. Cl.⁵ .................... A61M 5/20; A61M 5/32
[52] U.S. Cl. .................... 604/134; 604/135; 604/136; 604/192; 604/194
[58] Field of Search ............ 604/95, 110, 130–136, 604/138–139, 156–158, 192–196, 198–206, 218, 232; 128/D1

[56] References Cited

U.S. PATENT DOCUMENTS

| | | |
|---|---|---|
| 3,882,863 | 5/1975 | Sarnoff et al. . |
| 4,378,015 | 3/1983 | Wardlaw . |
| 4,445,510 | 5/1984 | Rigby . |
| 4,529,403 | 7/1985 | Kamstra . |
| 4,624,660 | 11/1986 | Mijers et al. . |
| 4,661,098 | 4/1987 | Bekkering et al. . |
| 5,085,641 | 2/1992 | Sarnoff et al. ............ 604/134 |
| 5,135,510 | 8/1992 | Maskiewicz et al. .......... 604/195 |

Primary Examiner—Randall L. Green
Assistant Examiner—A. Zuttarelli
Attorney, Agent, or Firm—Stevens, Davis, Miller & Mosher

[57] ABSTRACT

The present invention relates to an injection device for the automatic injection of at least one injection liquid, comprising an assembly of a discharge mechanism, a cartridge holder and a cartridge slidably accommodated in the cartridge holder, the discharge mechanism comprising an outer sleeve wherein the cartridge holder is slidably adapted. A protective cover is provided on the front of the device, covering the front portions of the cartridge holder and the outer sleeve in such a manner, that unintentional backward movement of the cartridge holder in the outer sleeve, resulting in activation of the device, is prevented.

20 Claims, 2 Drawing Sheets

INJECTION DEVICE

FIELD OF THE INVENTION

The invention relates to an injection device for the automatic injection of at least one injection liquid, comprising an assembly of a discharge mechanism, a cartridge holder and a cartridge slidably accommodated in the cartridge holder;

the discharge mechanism comprising an outer sleeve that is open at one end, a plunger that is movable in the sleeve, a coil spring that acts on said plunger to move same towards the open end of the sleeve, and a locking means that cooperates with said plunger to prevent undesired movement of the plunger;

the cartridge holder being slidably adapted within said outer sleeve to allow restricted backward telescopic movement relative thereto, thereby moving the locking means out of its retaining engagement with said plunger;

the cartridge comprising:

(a) a glass ampoule having an injection needle connected to the front thereof and being open-ended at the opposite end thereof, a portion of said ampoule remote from the needle comprising a hollow cylinder having an at least substantially uniform inside diameter, (b) a piston adapted for movement by the plunger sealingly provided in said cylinder, (c) at least one injection liquid provided in said ampoule between the piston and a sealing member at the front of the cartridge, and (d) a needle sheath covering the needle to keep the needle in a sterile condition prior to use of the device.

BACKGROUND OF THE INVENTION

Such an injection device is disclosed in U.S. Pat. No. 3,882,863 and also, in improved embodiments, in European patent specifications 107874 and 186916. The invention encompasses in addition an injection device for accommodating more than one injection liquid, a plural-compartment injection device, wherein the injection liquids can be injected successively by passing through a suitable by-pass means, e.g. as described in European patent specification 72057.

The above known automatic injection devices or auto-injectors have been developed in particular for use by soldiers in an emergency situation, viz. after having been exposed to a battle gas of the enemy, e.g. a nerve gas. Such injection devices are usually stored for many years at a time (a shelf life of at least 5 years is required by the authorities), after which the device must function reliably at the critical instant. When the injection is required, this must generally be administered through the battle-dress. It will be obvious from the above, that a powerful spring must be used and that, in connection therewith and in relation to the required long storage stability, loaded parts such as the plunger should be manufactured from rigid materials with a high aging resistance, preferably from a suitable metal. In addition, these known auto-injectors are rather complicated due to the great number of cooperating parts, and their friendliness to the user is not fully satisfactory due to their heavy impact after activation.

SUMMARY OF THE INVENTION

It is the object of the present invention to provide an automatic injection device which is in particular intended for civil use, e.g. by patients suffering from certain chronic diseases such as migraine, diabetes, allergies, etc., or by persons requiring immediate medical treatment after accute incidents, such as poisonings, e.g. by snake-bites or by wasp-stings, and traffic accidents. It will be readily appreciated that such an injection device should be of a simplified construction to allow easy and inexpensive assemblage and of a minimum number of parts, which can be easily moulded from synthetic material using simple mould configurations. In this manner the costs of production can be kept low. At the same time, the device should be friendly to the user, i.e. compact in order to be easily carried about by the user, and simple in activation and operation.

An automatic injection device for the above purpose is described in U.S. Pat. No. 4,378,015. The reliability of this device, however, is not satisfactory. In particular, the connection of the injection needle, viz. in a ferrule disposed via a crushable foam column on a pedestal, is not sufficiently stable and solid to warrant a proper operation of the device. In addition, the structure leaves much injection liquid behind in the device after use, which will be discarded together with the device. Moreover, the piston should be punctured by the injection needle to allow the injection liquid to be injected; this implies a great risk of rubber particles (particulate matter) in the injection liquid. Further, the sterility of the injection needle is not guaranteed.

More in particular, it is the object of the present invention to provide an automatic injection device, which conforms to the above-defined requirements but which does not have the structural disadvantages presented by the device known from the above-mentioned U.S. Pat. No. 4,378,015. Moreover, such a device should preferably allow the application of usual constructive parts, in particular of conventional syringe parts, to decrease the costs of production. In addition, it is very important that after use the device should permit to be rendered harmless in a convenient manner.

This object can be achieved with an automatic injection device as defined in the opening paragraph, which is characterized according to the present invention, in that a protective cover is provided on the front of the device, covering the front portions of the cartridge holder and the outer sleeve in such a manner, that unintentional backward movement of the cartridge holder in the sleeve is prevented.

The above-defined protective cover, to be used as an essential safety means for the injection device of the invention, prevents accidental activation of the device and forms an inexpensive provision for this purpose. Said cover is preferably closed at its front and at its side wall to constitute a dust-proof seal for the front portion of the injection device. Moreover, said protective cover can easily and simply be replaced after use of the device, thus covering the exposed injection needle and in this manner rendering the injection device harmless after use.

In a favorable embodiment the protective cover, to be used for the injection device of the present invention, is provided with an inwardly extending circumferential ridge abutting against the front edge of the outer sleeve, thereby preventing said outer sleeve from moving forward relative to the cartridge holder. Such a circumferential ridge may be constituted conveniently by means of a shoulder-like joint of two aligned sleeve-like portions of the protective cover, the front of which having a reduced internal diameter.

Preferably, and in particular in view of the high demands made upon such a device, the injection device of the present invention is characterized in that the outer sleeve comprises a closed rear portion, a circumferentially closed front portion and an intermediate portion, said intermediate portion being provided with longitudinal slots, to allow the side wall of said portion to be pushed outwards, said intermediate portion comprising a frusto-conical backward tapering part, and the inner wall of said intermediate portion being provided with a plurality of circumferentially positioned, inwardly extending projections, which retainingly engage the front of the plunger and in this manner form the locking means for said plunger;

said device being further characterized, in that the cartridge holder comprises two concentric sleeve-like portions, a first portion accommodating said cartridge and a second, wider portion having such dimensions that the outer sleeve can be slidably adapted around it and being provided with means to allow its restricted backward telescopic movement therein, said wider portion terminating with its backward extension in a rear edge bearing against the inner wall of the frusto-conical part of the outer sleeve's intermediate portion in such a manner, that a backward movement of the cartridge holder relative to the outer sleeve results in an outward push of said intermediate portion by said elongation's rear edge, thus allowing the plunger to be released from its retaining engagement with said projections on the inner wall of said intermediate portion.

The device of the present invention in its above-defined embodiment is pre-eminently suitable for its intended use, is of a simplified construction and can easily be assembled from conventionally available parts. Activation and operation of the device are convenient and reliable. After the protective cover has been removed, the injection device can be activated by pressing the device with its front face on or against the place of the body where the injection should be administered, resulting in said restricted backward telescopic movement of the cartridge holder in the outer sleeve and release of the plunger, by which the injection device is activated. The operation of the device is explained in more detail hereinafter. Said means at the wider portion of the cartridge holder which in conjuction with means provided in or on the outer sleeve, in particular at the outer sleeve's front portion, may favourably comprise a plurality of outwardly extending cams on one of these portions and an equal number of matched grooves or a circumferentially recessed groove in the other portion, thus allowing their mutual restricted shift.

As an additional safety for the injection device in its above preferred embodiment the protective cover is provided with a backward extending sleeve, fittingly enclosing with its backmost portion the intermediate portion of the outer sleeve, and terminating in an inwardly bent annular rear edge. In this favourable embodiment said backmost portion of the sleeve of the protective cover, enclosing the resilient intermediate portion of the outer sleeve, prevents this latter portion from bulging out and consequently forms an additional prevention against unintentional activation of the injection device. Both shift of the cartridge holder relative to the outer sleeve and outward push of the cartridge holder's intermediate portion, resulting in release of the plunger and activation of the injection device, are impossible before the protective cover has been removed.

To further safeguard the cartridge from accidentally moving forward in the cartridge holder, for instance as a result of an outward impact or a fall of the device, the first portion of the cartridge holder, accommodating the cartridge, is preferably internally provided with an annular ridge or a plurality of circumferentially positioned projections, situated just in front of the glass ampoule and thus forming an abutment for the ampoule shoulder prior to use of the device. When the device is used, however, these projections can easily be overridden due to the resiliency of the cartridge holder wall, preferably manufactured from a synthetic material. In addition, the inner wall of said first portion of the cartridge holder is preferably provided with an annular inward ridge, functioning as an abutment for stopping the actuated cartridge in its foremost position after activation of the injection device.

In a favourable embodiment the plunger comprises two concentric portions, the inner portion with its front end operatively engaging the piston, and the outer portion, which is surrounded by the coil spring, with its front end engaging the projections on the inner wall of the outer sleeve's intermediate portion, said coil spring being compressed between an outward flange at the front end of said outer portion and the closed back wall of the outer sleeve's rear portion. It has been found, that such a configuration of the plunger allows an easy assemblage of the discharge mechanism and the application of a coil spring with a relatively small spring force. The bipartite construction of the plunger allows the coil spring to be assembled at the outside of the plunger's outer portion. Therefore a coil spring can be used having a relatively large diameter and hence with a relatively small spring force. Such a coil spring permits the discharge mechanism, in particular the plunger thereof, to be constructed from a synthetic material, less expensive and easier in manufacturing, viz. by injection moulding.

It is an additional feature of the present invention, that the protective cover to be used for the injection device of the present invention is constructed in such a manner that it allows the attachment of means that can remove the needle sheath from the injection needle simultaneously with the detachment of the protective cover. For this purpose the protective cover is internally provided with at least two resilient lugs, which are connected to a nose portion of said protective cover and extend backwards within said cover in such a manner, that they grippingly engage the needle sheath, thus allowing said sheath to be removed simultaneously with the detachment of the protective cover from the device. Said lugs may be provided with barbs at their sides engaging the needle sheath, to improve their grip. In a favourable embodiment the needle sheath is manufactured from a resilient material, e.g. a rubber, to allow easy gripping by the lugs. A rubber needle sheath can equally constitute a sealing member for the injection liquid at the front of the cartridge, in case the injection needle and the needle sheath are mutually dimensioned in such a manner, that the tip of the needle is sealingly closed by the rubber needle sheath. Other examples of suitable sealing members at the front of the cartridge are stoppers which can be passed by the injection liquid upon use of the device (see e.g. the above-mentioned European patent 72057) and membranes, attached in the front portion of the cartridge (see e.g. the above mentioned U.S. Pat. No. 3,882,863). Alternatively, said needle sheath may be manufactured from a rigid synthetic material. In that case the outer surface of the sheath is preferably provided with transverse ribs to improve the gripping by the lugs. In a favorable embodiment of the protective cover provided with said resilient lugs, the nose portion of the protective cover and the resilient lugs constitute a room for accommodating the front portion of the needle sheath, thus allowing replacement of the protective cover after use of the device. This feature will be explained in more detail hereafter. After use of the device, the injection needle protrudes from the front of the injection device. Replacement of the protective cover simultaneously with replacement of the needle sheath, clamped within this cover, is a highly advantageous precautionary measure. To permit replacement of both cover and sheath, however, this sheath should have sufficient room to shift forward within the nose portion of the protective cover.

As mentioned before, it is advantageous to construct the injection device in such a manner, that a conventional, manually operated, pre-filled injection syringe, of course without a piston rod, can be accommodated in the device to function as the cartridge.

BRIEF DESCRIPTION OF THE DRAWINGS

The invention will now be described in greater detail with reference to a preferred embodiment which is shown in the drawings, in which.

DETAILED DESCRIPTION OF THE INVENTION

Figure 1:
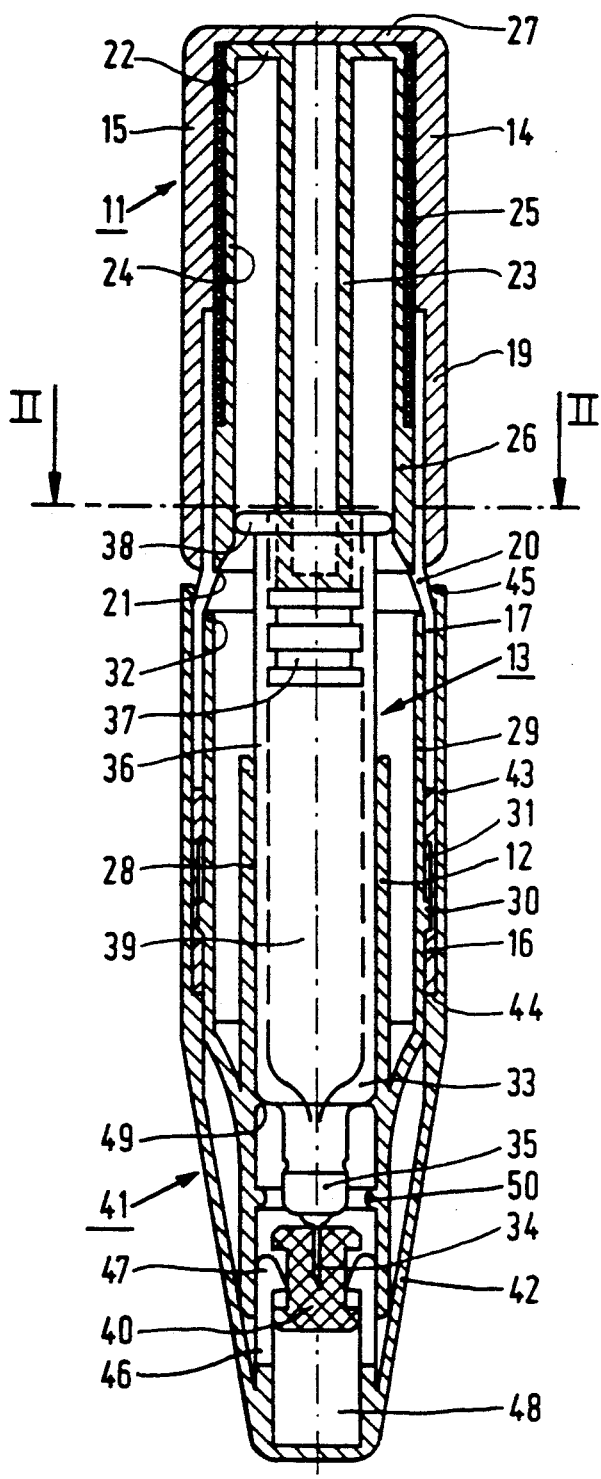
FIG. 1 is a longitudinal sectional view of an injection device according to the present invention.
Figure 2:
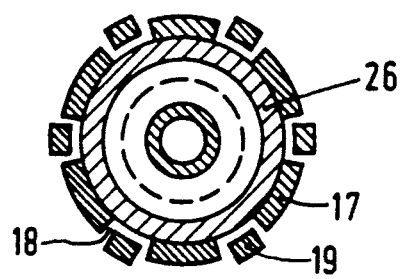
FIG. 2 is a cross-sectional view of the device shown in FIG. 1, taken on the line II—II in FIG. 1 and viewed in the direction of the needle.

The injection device shown in FIGS. 1 and 2 comprises a discharge mechanism, generally denoted with 11, a cartridge holder 12 and a cartridge, generally denoted with 13 and slidably accommodated in the cartridge holder. The discharge mechanism comprises an outer sleeve 14, which is open at its forward end, and which comprises a closed rear portion 15, a circumferentially closed front portion 16 and an intermediate portion 17. Said intermediate portion is provided with longitudinal slots 18 and a plurality of strengthening ribs 19, and comprises a frusto-conical backward tapering part 20. The inner wall of the intermediate portion is provided with a plurality of circumferentially positioned inwardly extending projections 21, which together form an interrupted annular abutment for the plunger (see further). The discharge mechanism further comprises a plunger 22, comprising two concentric portions, the inner portion 23 engaging the piston and the outer portion 24 engaging with its front end the projections 21 on the inner wall of the outer sleeve. The outer portion of the plunger is surrounded by a coil spring 25, compressed between an outward flange 26 at the front of said outer portion and the closed back wall 27 of the outer sleeve.

The cartridge holder 12 comprises two concentric sleeve-like portions, a first portion 28 accommodating the cartridge, and a second, wider portion 29, slidably telescoping within the outer sleeve. Said wider portion is provided with at least two outwardly extending cams 30, fitting in a matched circumferential groove 31 recessed in the outer sleeve's front portion 16. The wider portion 29 of the cartridge terminates with its backward extension in a rear edge 32 bearing against the inner wall of the frusto-conical part 20 of the outer sleeve's intermediate portion. The cartridge holder is internally provided with a plurality of circumferentially positioned projections 49 for preventing the cartridge from an unintentional forward movement relative to the cartridge holder, e.g. by a shock, and with an annular abutment 50 for stopping the actuated cartridge in its foremost position upon use of the device.

The cartridge is a conventional, manually operated, prefilled injection syringe without piston rod and comprises a glass ampoule 33 having an injection needle 34 connected to the front thereof. At its front the ampoule is narrowed to a spout-shaped member 35, in the central aperture of which the needle is sealingly fixed with its backward portion, e.g. by glueing. In an equally favorable embodiment the needle is connected to the ampoule by means of a separate needle holder. The ampoule comprises a hollow cylinder 36, wherein a piston 37 is sealingly provided. The piston engages the front of the plunger's inner portion 23. The ampoule cylinder terminates at its rear end in an outwardly extending flange 38 (i.e. the finger grip of the syringe), movable within the plunger's outer portion 24. The ampoule comprises an injection liquid 39 sealingly enclosed between the piston and a needle sheath 40 of a resilient material, preferably a rubber, sealing the needle tip.

The device is provided with a protective cover generally referenced by 41, constituting a dust-proof seal for the front portion of the injection device. Between the nose portion 42 and the backward extending sleeve 43, having a thinned side-wall, a shoulder 44 is formed, constituting an abutment for the front edge of the outer sleeve's front portion 16. In this manner said outer sleeve is prevented from moving forward relative to the cartridge holder. The backward extending sleeve 43 of the protective cover fittingly encloses with its backmost portion the intermediate portion 17 of the outer sleeve, and terminates in an inwardly bent annular rear edge 45. In this manner said backmost portion of sleeve 43 prevents this intermediate portion of the outer sleeve from bulging out and, as a consequence, from unintentional release of the plunger. The nose portion 42 of the protective cover is internally provided with four resilient lugs 46, with their detent heads 47 engaging behind a thickened front portion of the needle sheath 40. In this manner the needle sheath is removed simultaneously with the detachment of the protective cover from the injection device. The nose portion of the protective cover constitutes a room 48 in front of the needle sheath, its use being explained hereinafter.

The operation of the injection device of the patent invention will be explained in greater detail with reference to the accompanying FIGS. 3 to 7. Equal or corresponding parts are denoted with the reference numerals used in FIGS. 1 and 2.

Figure 4:
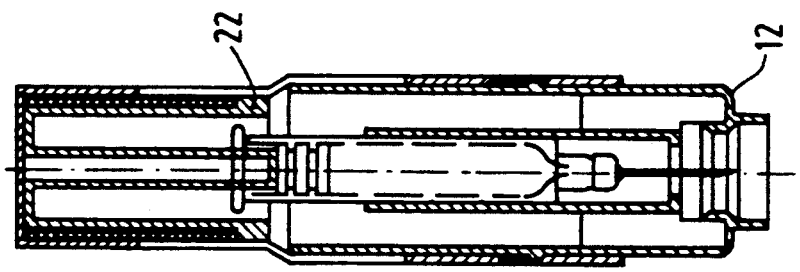
Figure 3:
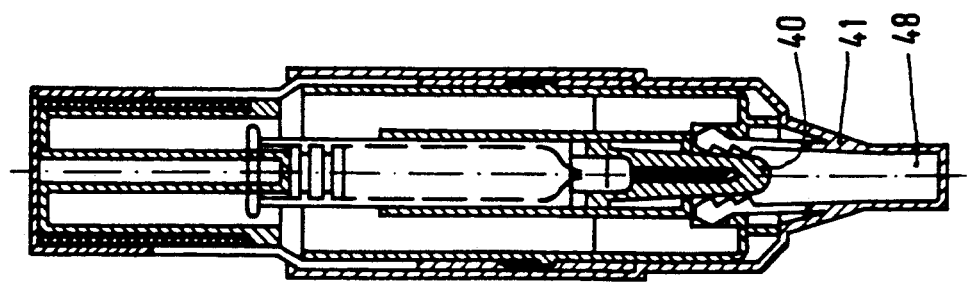

FIG. 3 shows the injection device before use and therefore corresponds with the situation presented in FIG. 1. Detachment of the protective cover 41 results in simultaneous removal of needle sheath 40; this situation is shown in FIG. 4. The injection device is now ready for use and is placed with its front, i.e. the front portion of the cartridge holder 12, on the spot where the injection should be given, and pressed. By doing this the cartridge holder moves slightly backwards relative to the outer sleeve 14.

The backward movement of the cartridge holder's wider portion 29, bearing with its rear edge against the inner wall if the frusto-conical part 20 of the outer sleeve, results in an outward push of said part of the outer sleeve and in a release of the plunger 22 from its retaining engagement with the projections on the inner wall of said outer sleeve's part. Thereupon the plunger moves forward under the influence of the compressed coil spring (see the arrow in FIG. 5). The plunger pushes the cartridge 13 forward until in its ultimate forward position the movement of the ampoule cylinder is stopped by the annular abutment 50 of the cartridge holder. During the forward movement of the cartridge in the cartridge holder the projections 49 are overridden by the ampoule cylinder. The injection needle 34 has now penetrated the skin.

Figure 7:
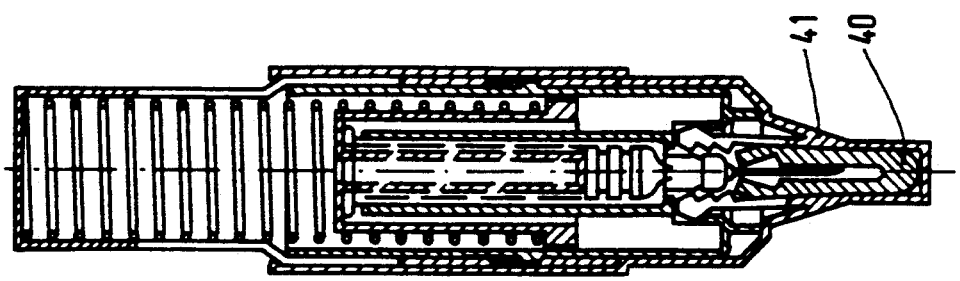
FIGS. 3 to 7 illustrate the operation of a comparable injection device, slightly different from the injector shown in FIG. 1.
Figure 6:
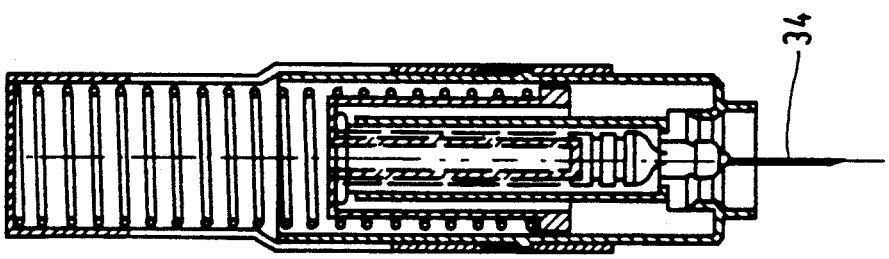
Figure 5:
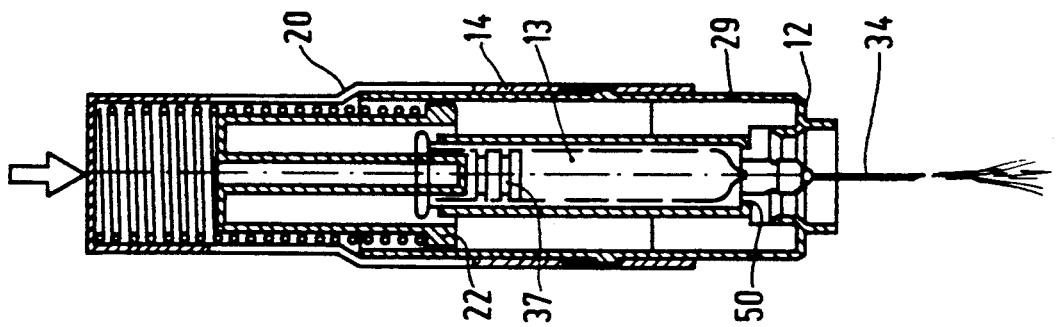

Now the piston 37 is moved forward in the ampoule cylinder by the plunger, equally under influence of the releasing coil spring, and the actual injection starts, i.e. the injection liquid is injected into the patient's body. After all injection liquid has been injected, as is visualized in FIG. 6, the protective cover with needle sheath is replaced as a precautionary measure. During this action, the needle sheath shifts forwards till within the empty room 48 in the protective cover. This situation is shown in FIG. 7.

I claim:

1. An injection device for automatic injection of at least one injection liquid, said device having a front and comprising an assembly of a discharge mechanism, a cartridge holder and a cartridge slidably accommodated in the cartridge holder;
the discharge mechanism comprising an outer sleeve that is open at one end, a plunger that is movable in the sleeve, a coil spring that acts on said plunger to move said plunger towards the open end of the sleeve, and a locking means that cooperates with said plunger to prevent undesired movement of the plunger;
the cartridge holder being slidably adapted within said outer sleeve to allow restricted backward telescopic movement relative thereto, thereby moving the locking means out of its retaining engagement with said plunger;
the cartridge comprising:
(a) a glass ampoule comprising a front and an end opposite the front, said front of said ampoule being proximate the front of said device, said glass ampoule having an injection needle connected to the front thereof and being open-ended at the opposite end thereof, a portion of said ampoule remote from the needle comprising a hollow cylinder having an at least substantially uniform inside diameter,
(b) a piston adapted for movement by the plunger sealingly provided in said cylinder,
(c) at least one injection liquid provided in said ampoule between the piston and a sealing member at a front of the cartridge, and
(d) a needle sheath covering the needle to keep the needle in a sterile condition prior to use of the device;
wherein a protective cover is provided on the front of the device, said cover covering front portions of the cartridge holder and the outer sleeve in such a manner that unintentional backward movement of the cartridge holder in the outer sleeve is prevented.

2. Injection device as claimed in claim 1, wherein the protective cover is provided with an inwardly extending circumferential ridge abutting against the front edge of the outer sleeve, thereby preventing said outer sleeve from moving forward relative to the cartridge holder.

3. Injection device as claimed in claim 1 or 2, wherein the outer sleeve comprises a closed rear portion, a front portion and an intermediate portion,
said intermediate portion being provided with longitudinal slots, to allow a side wall of said portion to be pushed outward,
said intermediate portion comprising a frusto-conical backward tapering part, and
an inner wall of said intermediate portion being provided with a plurality of circumferentially positioned, inwardly extending projections, which retainingly engage a front of the plunger and form the locking means for said plunger;
wherein the cartridge holder comprises two concentric sleeve-like portions, a first portion accommodating said cartridge and a second, wider portion having such dimensions that the outer sleeve can be slidably adapted around it and being provided means to allow its restricted backward telescopic movement therein, said wider portion terminating with its backward extension in a rear edge bearing against the inner wall of the frusto-conical part of the outer sleeve's intermediate portion in such a manner that a backward movement of the cartridge holder relative to the outer sleeve results in an outward push of said intermediate portion by said elongation's rear edge, thus allowing the plunger to be released from its retaining engagement with said projections on the inner wall of said intermediate portion.

4. Injection device as claimed in claim 3, wherein the cartridge is a manually operated, prefilled injection syringe without a piston rod.

5. Injection device as claimed in claim 3, wherein the first portion of the cartridge holder, accommodating the cartridge, is internally provided with a plurality of circumferentially positioned projections or with an annular ridge for preventing the cartridge from a forward movement within the cartridge holder prior to use of the device, and with an annular abutment for stopping the actuated cartridge in its foremost position upon use of the device.

6. Injection device as claimed in claim 3, wherein the protective cover is provided with a backward extending sleeve, fittingly enclosing with its backmost portion the intermediate portion of the outer sleeve, and terminating in an inwardly bent annular rear edge.

7. Injection device as claimed in claim 6, wherein the plunger comprises two concentric portions, an inner portion with its front end operatively engaging the piston, and an outer portion, which is surrounded by the coil spring, with its front end engaging the projections on the inner wall of the outer sleeve's intermediate portion, said coil spring being compressed between an outward flange at the front of said outer portion and the closed back wall of the outer sleeve's rear portion.

8. Injection device as claimed in claim 7, wherein the cartridge is a manually operated, prefilled injection syringe without a piston rod.

9. Injection device as claimed in claim 6, wherein the protective cover is internally provided with at least two resilient lugs, which are connected to a nose portion of said protective cover in such a manner, that they grippingly engage a needle sheath, allowing said sheath to be removed simultaneously with detachment of the protective cover from the device.

10. Injection device as claimed in claim 9, wherein the nose portion of the protective cover and the resilient lugs constitute a room for accomplishing a front portion of the needle sheath, thus allowing replacement of the protective cover after use of the device.

11. Injection device as claimed in claim 6, wherein the cartridge is a manually operated, prefilled injection syringe without a piston rod.

12. Injection device as claimed in claim 3, wherein the plunger comprises two concentric portions, an inner portion with its front end operatively engaging the piston, and an outer portion, which is surrounded by the coil spring, with its front end engaging the projections on the inner wall of the outer sleeve's intermediate portion, said coil spring being compressed between an outward flange at the front of said outer portion and the closed rear portion of the outer sleeve.

13. Injection device as claimed in claim 12, wherein the protective cover is internally provided with at least two resilient lugs, which are connected to a nose portion of said protective cover in such a manner, that they grippingly engage the needle sheath, thus allowing said sheath to be removed simultaneously with detachment of the protective cover from the device.

14. Injection device as claimed in claim 13, wherein the nose portion of the protective cover and the resilient lugs constitute a room for accommodating a front portion of the needle sheath, thus allowing replacement of the protective cover after use of the device.

15. Injection device as claimed in claim 12, wherein the cartridge is a manually operated, prefilled injection syringe without a piston rod.

16. Injection device as claimed in claim 3, wherein the protective cover is internally provided with at least two resilient lugs, which are connected to a nose portion of said protective cover in such a manner, that they grippingly engage the needle sheath, thus allowing said sheath to be removed simultaneously with detachment of the protective cover from the device.

17. Injection device as claimed in claim 16, wherein the nose portion of the protective cover and the resilient lugs constitute a room for accommodating the front portion of the needle sheath, thus allowing replacement of the protective cover after use of the device.

18. Injection device as claimed in claims 1 or 2, wherein the protective cover is internally provided with at least two resilient lugs, which are connected to a nose portion of said protective cover in such a manner, that they grippingly engage the needle sheath, thus allowing said sheath to be removed simultaneously with detachment of the protective cover from the device.

19. Injection device as claimed in claim 18, wherein the nose portion of the protective cover and the resilient lugs constitute a room for accommodating the front portion of the needle sheath, thus allowing replacement of the protective cover after use of the device.

20. Injection device as claimed in claims 1 or 2, wherein the cartridge is a manually operated, prefilled injection syringe without a piston rod.

* * * * *